US00RE36221E

United States Patent [19]

Breard et al.

[11] E Patent Number: Re. 36,221

[45] Reissued Date of Patent: Jun. 1, 1999

[54] FLEXIBLE INTER-VERTEBRAL STABILIZER AS WELL AS PROCESS AND APPARATUS FOR DETERMINING OR VERIFYING ITS TENSION BEFORE INSTALLATION ON THE SPINAL COLUMN

[76] Inventors: Francis Henri Breard, 13, rue Friant, 75014 Paris; Henry J. M. Graf, 12, Quai Jules Courmont, 69002 Lyons, both of France

[21] Appl. No.: 08/648,397

[22] Filed: May 15, 1996

Related U.S. Patent Documents

Reissue of:

[64] Patent No.: 5,092,866
Issued: Mar. 3, 1992
Appl. No.: 08/474,468
Filed: Feb. 2, 1990

U.S. Applications:

[63] Continuation of application No. 08/203,000, Feb. 28, 1994, abandoned.

[30] Foreign Application Priority Data

Feb. 3, 1989 [FR] France ..... 89 01445

[51] Int. Cl.[6] ..... A61B 17/70; A61F 2/44

[52] U.S. Cl. ..... 606/61; 623/17

[58] Field of Search ..... 606/61, 90, 60; 623/13, 17

[56] References Cited

U.S. PATENT DOCUMENTS

| | | | |
|---|---|---|---|
| 1,907,495 | 5/1933 | Brunski | 248/497 |
| 3,997,138 | 12/1976 | Crock et al. | 606/61 X |
| 4,041,939 | 8/1977 | Hall . | |
| 4,078,559 | 3/1978 | Nissinen | 606/61 |
| 4,275,490 | 6/1981 | Bivins | 606/72 X |
| 4,570,618 | 2/1986 | Wu . | |
| 4,632,097 | 12/1986 | Brooks | 602/16 |
| 4,641,636 | 2/1987 | Cotrel . | |
| 4,733,657 | 3/1988 | Kluger | 606/61 |
| 4,743,260 | 5/1988 | Burton | 623/17 |
| 4,773,910 | 9/1988 | Chen et al. . | |
| 4,790,850 | 12/1988 | Dunn et al. . | |
| 4,805,602 | 2/1989 | Puno et al. . | |
| 4,836,196 | 6/1989 | Park et al. . | |
| 4,955,910 | 9/1990 | Bolesky . | |

FOREIGN PATENT DOCUMENTS

| | | | |
|---|---|---|---|
| 00159007 | 3/1984 | European Pat. Off. . | |
| 0260970 | 3/1988 | European Pat. Off. | 623/13 |
| 0322334A1 | 12/1988 | European Pat. Off. . | |
| 0 348 272 | 12/1989 | European Pat. Off. . | |
| 2 309 201 | 12/1976 | France . | |
| 2 596 641 | 10/1987 | France . | |
| 2 623 085 | 8/1994 | France . | |
| 3 625 542 | 11/1987 | Germany . | |
| 3 807 335 | 9/1989 | Germany . | |
| 3 095 060 | 4/1988 | Japan . | |
| 7 610 576 | 9/1976 | Netherlands . | |

OTHER PUBLICATIONS

English translation of Netherlands patent to slot No. 7610576.

*Primary Examiner*—David H. Willse
*Attorney, Agent, or Firm*—Collard & Roe, P.C.

[57] ABSTRACT

The present invention relates to an inter-vertebral stabilizer having one or more flexible ligaments. Each flexible ligament can be engaged with two respective vertebrae and/or associated with two retaining elements, such as screws, each of which is suitable for being implanted in a respective vertebra. The present invention also relates to a process, and the associated apparatus, for determining or verifying the tension of such an inter-vertebral stabilizer before it is put into place on the spinal column. This process includes implanting, in each of the vertebrae concerned, a corresponding rigid rod extending outside the patient's body. The rods in each pair of adjacent rods are immobilized in an initial position. If the pain which is to be removed by the stabilizer persists, the process includes modifying the distance between the rods, then in immobilizing the rods in their new relative positions and in repeating the pain test. This cycle of operations is repeated, if necessary, until the pain disappears. The length to be allocated to the ligament is deduced from the distance then attained between the two rods.

17 Claims, 4 Drawing Sheets

FLEXIBLE INTER-VERTEBRAL STABILIZER AS WELL AS PROCESS AND APPARATUS FOR DETERMINING OR VERIFYING ITS TENSION BEFORE INSTALLATION ON THE SPINAL COLUMN

Matter enclosed in heavy brackets [ ] appears in the original patent but forms no part of this reissue specification; matter printed in italics indicates the additions made by reissue.

*This is a continuation of application Ser. No. 08/203,000, filed on Feb. 28, 1994, now abandoned, which is a reissue of application Ser. No. 07/474,468, filed on Feb. 2, 1990, now U.S. Pat. No. 5,092,866.*

The present invention relates to an inter-vertebral stabilizer to be installed between at least two vertebrae to correct defects in the spinal column.

Inter-vertebral stabilizers currently used to attenuate the often painful effects of diseases of the spinal column, such as scolioses, nucleus pulposus herniations or lumbar instabilities, take the form of metal plates or rods that are fixed to the vertebrae or to their spines, along the affected section of the spinal column, which has the drawback of completely immobilizing the vertebrae, hence of restricting or even completely preventing flexional or torsional movements of the patient's trunk.

The present invention proposes to overcome this drawback and, for that purpose, it provides an inter-vertebral stabilizer of a novel type which is characterized in that it comprises one or more flexible ligaments having an all-direction flexibility, each of them being provided with means for fastening it to two respective vertebrae and/or associated with two retaining elements, each of which can be implanted in a respective vertebra.

Advantageously, the flexible ligament has the general form of a closed loop or, alternatively, is provided with a ring or a closed loop at each end thereof, whereby the ends of each ligament constitute said fastening means through which said ligament can be fastened by hanging to a spine or any other protrusion of a respective vertebra. When retaining elements are provided, each of them, being preferably a screw, is advantageously formed with a free head for fastening a respective end of the corresponding ligament.

There is thus obtained a flexible or semi-elastic inter-vertebral stabilizer which, according to its mode of implantation, on one side only or on both sides of the spines of the vertebrae concerned, on the front face or the rear face thereof, with a single ligament or with several ligaments chained together or even crossed with each other, makes it possible to compensate for all sorts of defects or deformations of the spinal column by permitting sufficient clearance between the vertebrae not to hinder the patient in the flexional or torsional movements of his trunk.

Apart from this main advantage, the inter-vertebral stabilizer according to the invention is extremely simple to install: it suffices to engage the end of each ligament around for example two vertebral spines or two screws pre-implanted in the vertebrae.

To prevent any slipping of the ligament once it has been put in place, in the case where retaining elements, such as screws, are used, provision is also advantageously made for fitting onto each retaining element, a removable cap that is radially over-dimensioned in relation to the head of the retaining element. The same effect can be obtained by alternatively providing the head of each retaining element with a lateral projection for retaining the ligament.

Before putting the stabilizer in place on the spinal column, its tension, i.e. the length at rest of the, or of each, flexible ligament, will naturally have to be determined precisely in accordance with the seriousness of the defect to be corrected and, for this purpose, the present invention proposes a process comprising the steps which consist successively:

in making a surgical incision in the patient's body in front of each vertebra concerned for uncovering it, in implanting a rigid rod in each of the vertebrae concerned and at the point at which the corresponding ligament is to be fixed, with said rod extending out of the patient's body, in immobilizing the two rods of each pair of adjacent rods, at a predetermined distance from one another, and in the event where the pain, the cause of which is to be removed by the stabilizer, is persisting after a given time period has elapsed, in modifying the distance between the rods by a certain pitch, and then in immobilizing the latter in their new relative positions and in carrying out the pain test once again, this cycle of operations being repeated, if necessary, until the said pain disappears, the length at rest to be given to the ligament then being deduced from the value of the distance then attained between the two rods.

This process can also be implemented for verifying and modifying the tension of one or more ligaments already in place on the spinal column, when the patient experiences pain after a less or more long period of use.

Another object of the invention is to provide an apparatus for determining the tension of an inter-vertebral stabilizer according to the invention before it is put into place on the spinal column, the said apparatus being characterized in that it comprises a set of at least two rods each having an end for implantation in the corresponding vertebra, these rods being associated at least with a rigid link of adjustable length designed to join them together at a point remote from their implantation ends.

According to a preferred embodiment, the implantation end of each rod is constituted by an element having a head onto which is removably fitted an extension piece forming the remaining portion of the rod, designed to receive the rigid length-adjustable link.

Once the operation of determining the tension of the inter-vertebral stabilizer has been completed, the end elements of the rods, which will preferably be screws, can be advantageously held in place in the vertebrae to form the ligament retaining elements, and the ligament, after being produced to the length calculated using the process according to the invention, can easily be engaged around the said screws by sliding along the extension pieces before they are removed.

The rigid length-adjustable link can, for its part, take various forms, the simplest being that of a thin bar and two collars that can be fitted respectively onto the two rods and are provided with means for slidably supporting the bar between them, a bar locking member being provided on each collar.

Advantageously, the apparatus according to the invention further comprises an instrument for determining the length at rest of a ligament, which is formed by two crossed legs articulated on one another at their middle, the ends of the legs located on the same side of the articulation each having a substantially semi-circular contacting portion, which is applied onto the head of the corresponding retaining element. In this way, it is possible to determine between the other ends of the two legs of this instrument the length required for the ligament to be implanted, which can be measured using a graduated rule.

Embodiments of the inter-vertebral stabilizer according to the invention, together with a process and an apparatus for determining their tension, will now be described in greater detail, but non limitatively, with reference to the accompanying drawings, wherein.

Figure 1:
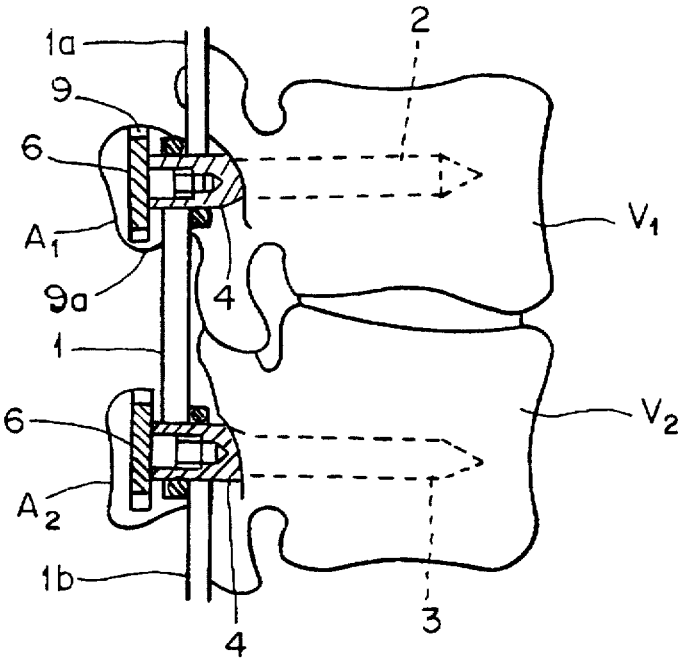
FIG. 1 shows a side view in partial cross-section of the inter-vertebral stabilizer according to the first embodiment of the invention.

FIG. 1 represents two adjacent vertebrae, V1, V2, of a patient's spinal column, linked by an inter-vertebral stabilizer according to the invention, which is composed of a flexible *or supple* ligament 1 in the form of a closed loop *or band* and of two screws 2,3 each implanted in a corresponding vertebra to retain ligament 1 between them, said ligament being simply engaged around the widened cylindrical heads 4 of the screws, emerging from the vertebrae. Ligament 1 is an artificial ligament made of "Dacron" (registered trade-mark) or of any other flexible plastics material, having an all-direction flexibility.

Figure 3A:
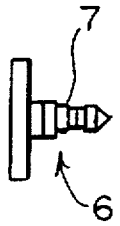
FIGS. 3a, 3b and 3c illustrate one of the ligament retaining elements of the stabilizer of FIG. 1.
Figure 3B:
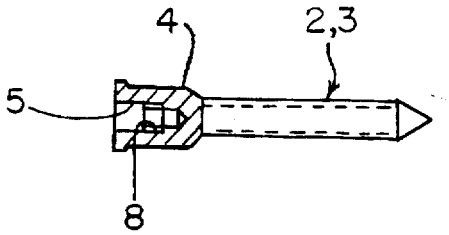
Figure 3C:
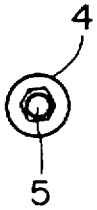

As more clearly shown in the longitudinal cross-sectional and front views of FIGS. 3b and 3c, the head 4 of each screw comprises an axial blind hole 5 having a hexagonal cross-section, in which a hexagonal key can be engaged in order to implant the screw in the corresponding vertebra.

After ligament 1 has been put into place around the screws thus implanted, hole 5 of each of said screws is closed using a flat circular cap or plug 6, shown alone in FIG. 3a, said cap, the diameter of which is substantially larger than that of head 4 of the screw, being screwed by means of a central pin 7 with a threaded end into a threaded bore 8 opening in the bottom of hole 5. To accomplish this screwing operation, use is made of a special key cooperating with two slots, 9,9a, formed on the periphery of each cap 6. Alternatively, each cap may be provided with a central hexagonal bore and screwed on the head 4 of the corresponding screw by using a hexagonal key engaged in this bore. By projecting radially right around the corresponding heads 4 of the screws, the two caps 6 preclude any likelihood of ligament 1 slipping off the said heads, as illustrated in FIG. 1.

The caps 6 are particularly useful when the inter-vertebral stabilizer according to the invention comprises several supplementary flexible ligaments, such as illustrated at 1a and 1b in FIG. 1, chained together with first ligament 1, on the vertebrae preceding and following the two designed by V1,V2, with the help of the same number of supplementary retaining screws.

Figure 2:
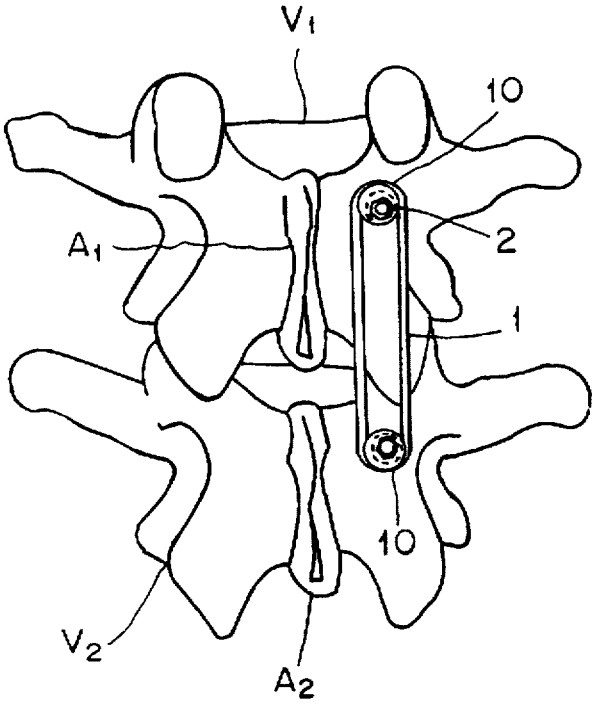
FIG. 2 is a front view of an inter-vertebral stabilizer according to the second embodiment of the invention.
Figure 4A:
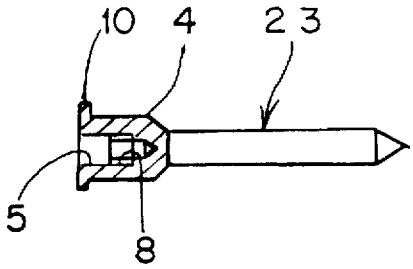
FIGS. 4a and 4b show, in longitudinal cross-sectional view and in front view respectively, one of the ligament retaining elements of the stabilizer of FIG. 2.
Figure 4B:
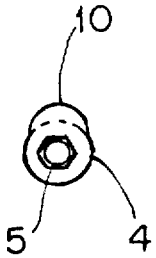

In the case illustrated in FIG. 2, in which only one ligament 1 in the form of a closed loop will have to be interposed between only two successive vertebrae V1,V2, the head 4 of each screw 2 or 3 can be provided alternatively with a lateral projection 10 of suitable height, as represented in profile and in front view in FIGS. 4a and 4b. In this case, it will be necessary first of all to implant the two screws 2,3 by orientating their projections 10 opposite one another so that ligament 1 can be then slid without any impediment around their heads 4, after which the screws will be given an additional half-turn to place projections 10 in their ligament retaining positions, as shown in FIG. 2.

The inter-vertebral stabilizer according to the invention makes it possible, according to its positioning, to combat numerous painful diseases affecting the spinal column. The stabilizer shown in FIGS. 1 and 2 is put into place on the rear face of vertebrae V1,V2 and on one side only of their spines A1,A2. However, depending on the type of disease to be treated, it is possible to use two stabilizers according to the invention, mounted on either side of vertebral spines A1,A2 or crossed between the two vertebrae V1,V2, on the front or rear face thereof. In all cases, however, it is necessary to determine the tension of the stabilizer, i.e. the length at rest of its ligament 1, accurately before it is installed, as a function of the seriousness of the defect to be corrected. For this purpose, the present invention proposes a process and an apparatus for its implementation, which will now be described with reference to FIGS. 5 to 8.

Figure 5:
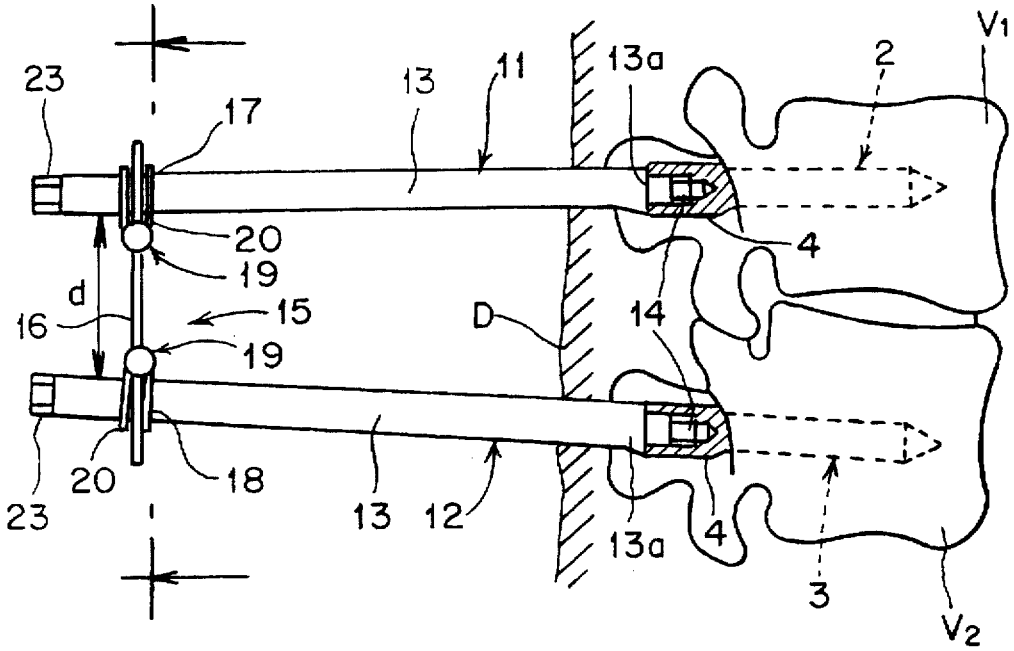
FIG. 5 is a side view, in partial cross-section, of the apparatus according to the invention, represented in use on two adjacent vertebrae.

As it can be seen, the basic accessories of this apparatus are two rigid rectilinear rods, 11,12, which are fixed in the respective vertebrae V1,V2 by their ends which, in the preferred embodiment represented in FIG. 5, are formed by screws 2,3 of what is to become the stabilizer. Each screw is implanted in the way described above after a local surgical incision has been made in the patient's back in front of each vertebra for uncovering it. Each rod 11,12 is completed by a cylindrical extension piece 13 having a threaded end 14, which is fitted onto the head 4 of the corresponding screw by screwing into its threaded bore 8 after removal of cap 6. For this purpose, the free opposite end of each extension piece 13 is provided with a hexagonal head 23 suitable for receiving a tightening key. It will also be noted that each extension piece 13 has a foot 13a which flares progressively until its diameter is substantially equal to that of the head of screw 4 onto which it is fitted.

The two rods 11,12 being thus implanted so as to extend out from the patient's back D, they are joined in the vicinity of their free ends 23 by a rigid link 15 of adjustable length and, by means of the latter, the distance between the rods is adjusted to a value that is predetermined as a function of the nature and the seriousness, previously diagnosed, of the defect to be corrected on the spinal column.

After the two rods have been thus immobilized in this initial position, the incisions in the patient's back are closed up and the patient is made to undergo a test which consists in verifying whether, at the end of a given period, possibly one to two days, the patient still experiences pain in the affected area of the spinal column. If this is the case, the spacing between rods 11,12 is slightly modified, generally for bringing them closer to one another (compression), by acting on the length of link 15, and the pain test is repeated over substantially the same period of time as before.

This dual operation will be repeated if necessary, preferably with a constant pitch of change in the spacing of rods 11, 12, until the patient no longer experiences any pain in the back. Once this result has been achieved, the length at test required for the ligament to be implanted between the vertebrae is measured or calculated with maximum accuracy.

In practice, the maximum number of successive cycles of verifying operations leading to the elimination of pain will be three and, if the pain proves to persist after these three cycles of operations, this will mean that the defect that causes it is not present in the pair of vertebrae tested and the process according to the invention will then have to be applied to the following pair of vertebrae or successively on the following pair(s) of vertebrae, until the pain disappears.

Of course, when several flexible ligaments are to be chained together, such as 1, 1a and 1b (FIG. 1), over a long section of the spinal column, the above described process will be applied simultaneously to all the successive vertebrae to be treated, using as many rods 11,12 as there are vertebrae and joining them two by two using length adjustable links such as 15.

Figure 6:
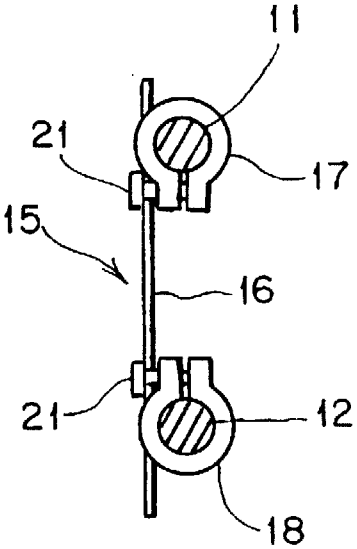
FIG. 6 is a cross-sectional view along line VI—VI of FIG. 5.

This link, which is more clearly represented in FIG. 6, is in fact formed here by a thin cylindrical bar 16 retained on two collars 17,18 each of which is fixed to a corresponding rod 11, 12 by means of a lock screw 19. Bar 16 is more precisely housed so as to be able to slide freely in a groove 20 of each of collars 17,18 and is locked therein, after the spacing of the rods has been adjusted, by head 21 of lock screw 19 of the corresponding collar. Alternatively, of course, link 15 can take the form of a device with threaded rods with reversed screws pitches, which could even be fitted with a system for directly measuring the spacing between rods 11,12.

The length to be allocated to the ligament can be derived, by a trigonometrical calculation, from the distance d measured, for example near link 15, between rods 11,12 immobilized in the right position. According to an additional feature of the invention, however, it is possible, as an alternative, to measure directly the length to be allocated to ligament 1 between heads 4 of screws 2,3 by using an instrument which will now be described, together with its mode of use, with reference to FIG. 7.

As it can be seen, this instrument 24 for determining the length of the ligament takes the general form of a "pair of scissors" and is more specifically, formed by two legs, 25,26, of the same length, which cross in their middle and are articulated on one another at their point of crossing by means of a lock screw 30. On the same side of this articulation 30, the ends of the two legs 25,26 carry a contacting piece, 28 or 29, which is substantially semi-circular and has a inner diameter slightly greater than that of the heads 4 of retaining screws 2,3. These contacting pieces 28 and 29 are facing each other and their inner arcuate face is flush with the inner side of the corresponding leg 25 or 26 of instrument 24. At their opposite ends, legs 25,26 are each provided with a ring, 31,32, to accommodate a finger.

To measure the length of the ligament using the said instrument 24, an incision is first made in the patient's back as far as vertebrae V1, V2 are uncovered. Then, after having loosened screw 30 and by holding instrument 24 in one hand by means of rings 31,32, each of contacting pieces 28 or 29 is placed on a respective rod 11 or 12 and the instrument is caused to slide along these rods until the contacting pieces are bearing on the ends of heads 4 of screws 2,3. Screw 30 is then re-tightened and, using a graduated rule 33, the distance between the free ends, 25a, 26a of legs 25,26 of instrument 24 is measured and the value of the length required for the ligament to be implanted between retaining screws 2,3 is thus obtained directly.

Figure 8:
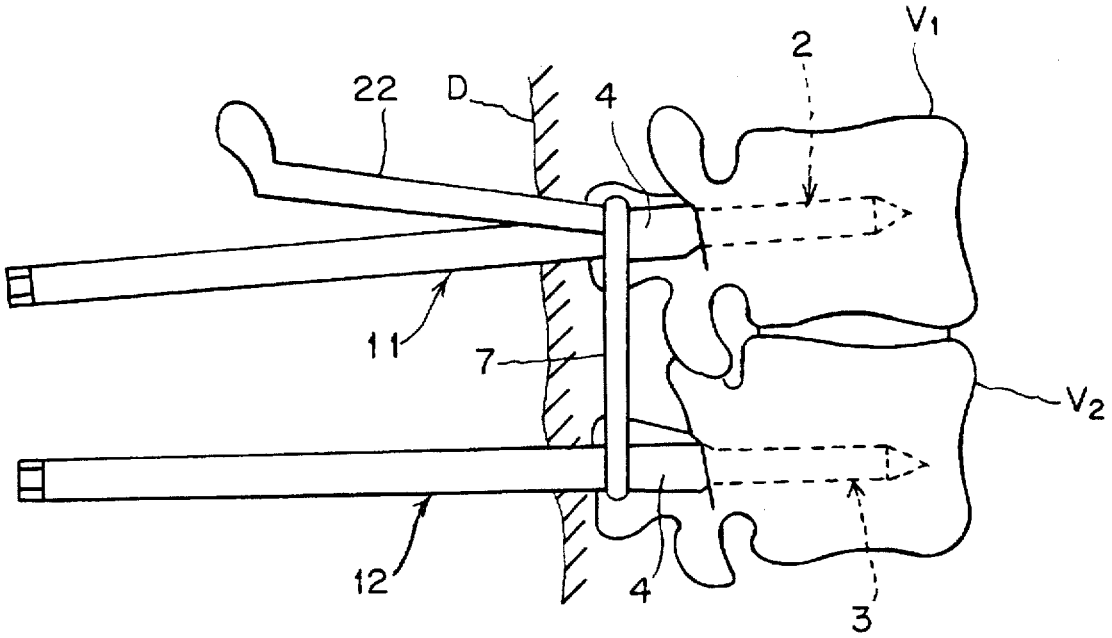
FIG. 8 represents the apparatus of FIG. 5 as used for the insertion of the flexible ligament around the retaining elements.
Figure 7:
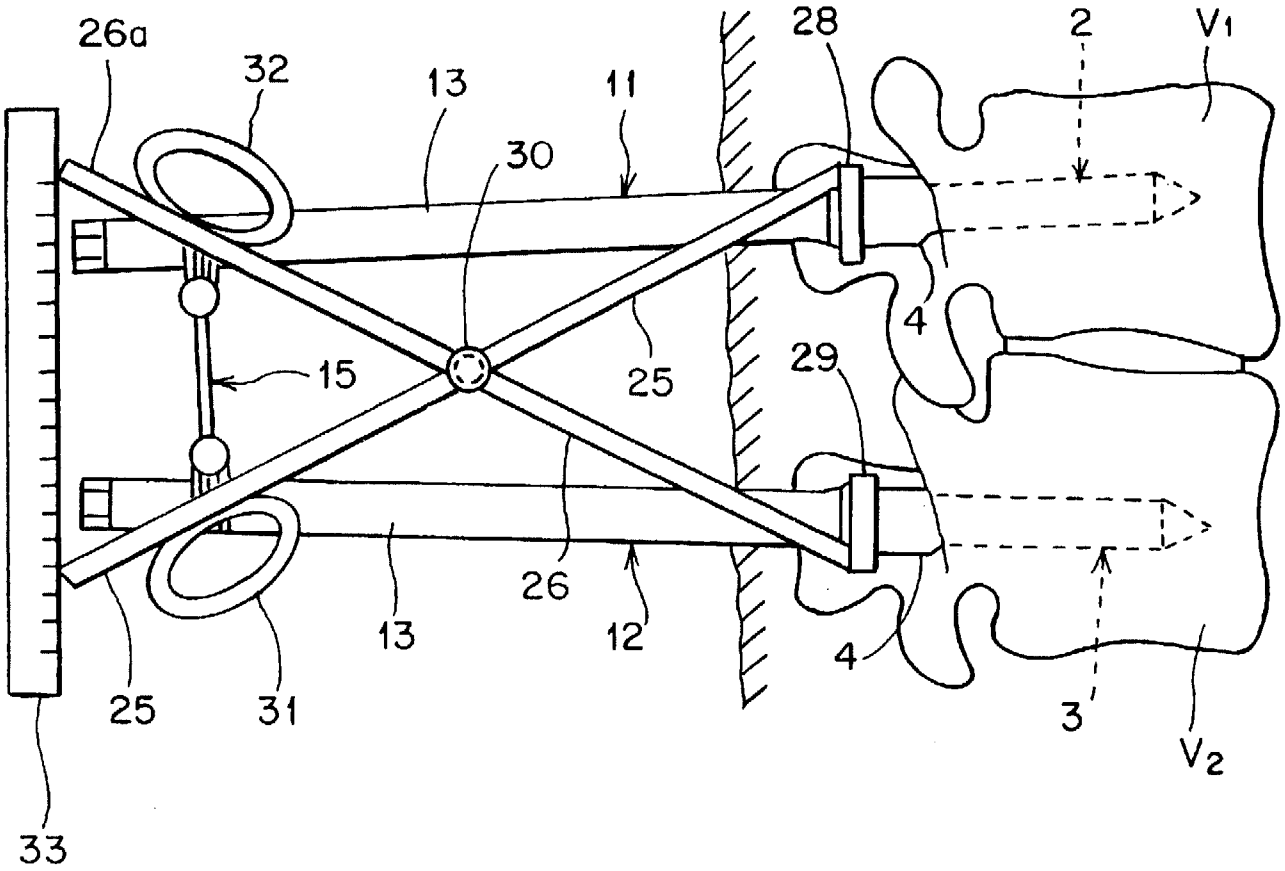
FIG. 7 illustrates in its position of use, a supplementary accessory of this apparatus, designed to determined the length at rest of the ligament.

After this length measurement, ligament 1 or each of ligaments 1, 1a, 1b to be implanted is prepared from a tubular artificial ligament which is flattened and sewn back on itself. After link 15 has been removed, the ligament thus formed into a loop is passed around the two extension pieces 13 and slid along them up to screws 2,3, around the heads 4 of which it is then engaged with the help, if necessary, of a special semi-cylindrically shaped tool 22, as shown in FIG. 8. Extension pieces 13 are then removed, caps 6 are screwed onto the heads of screws 2,3 (FIG. 1) or the latter are orientated in such a way as to place their projections 10 in ligament retaining position (FIG. 2); then the incisions in the patient's back is definitively closed up.

It goes without saying that numerous modifications can be made in the inter-vertebral stabilizer and in the apparatus that have just been described.

Figure 2A:
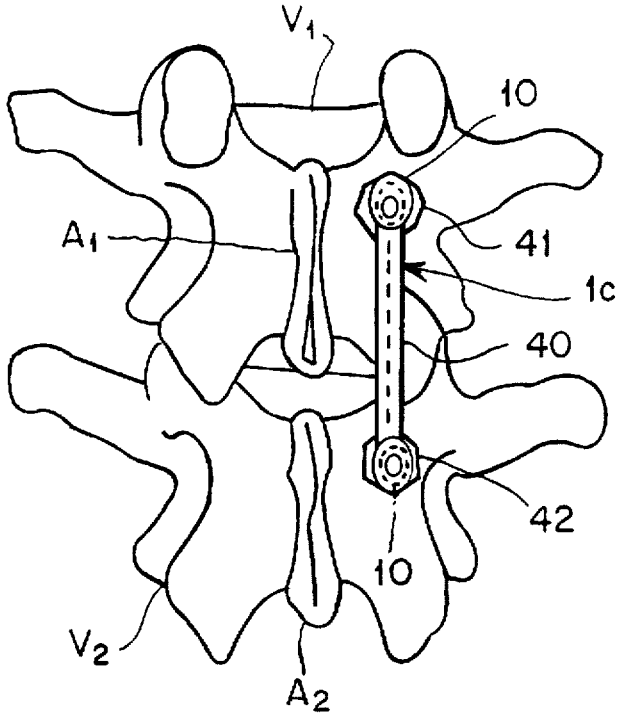
FIGS. 2a and 2b show alternative embodiments of the stabilizer of FIG. 2.

For instance, according to an alternative embodiment, shown on FIG. 2a, of the stabilizer of FIG. 2, the ligament 1c is in the form of a single segment 40 to each end of which a metallic ring 41 or 42 is attached, with which the ligament can be fastened by hanging over the head 4 of a respective retaining screw 2 or 3.

Figure 2B:
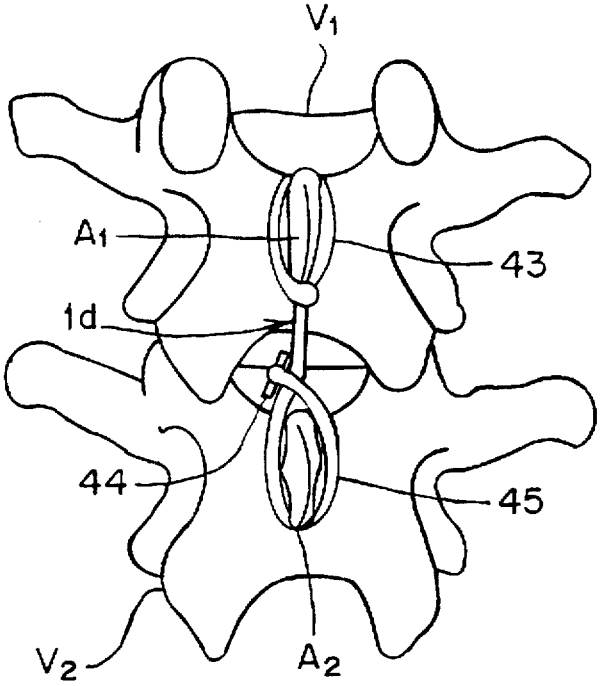

According to another alternative embodiment shown on FIG. 2b, the ligament 1d of the stabilizer, having the form of a closed loop, is passed through itself for defining a first end loop 43 which is engaged around the spine $A_1$ of a respective vertebra $V_1$. At its second end, the ligament 1d is placed around spine A2 of the lower vertebra $V_2$, then re-passed through itself for forming a second end loop 45 after insertion of a locking pin 44. Spines $A_1$ and $A_2$ here play the role of the retaining screws 2,3, but it goes without saying that ligament 1d of FIG. 2b can also be associated with such screws, as those 1 and 1c of FIGS. 2 and 2a. Inversely, ligaments 1 and 1c of FIGS. 2 and 2a can be fastened by an hanging connection directly over spines $A_1$ and $A_2$ of vertebrae $V_1$ and $V_2$, without the use of retaining screws, as the ligament 1d of FIG. 2d. Of course, a chained arrangement of a plurality of ligaments, as the one shown on FIG. 1, may also be obtained with the embodiments of FIGS. 2a and 2b, by means of pre-implanted retaining screws or by direct fastening over the spines of the vertebrae concerned.

For their part, screws 2,3 could be replaced by any other retaining element capable of being implanted in a vertebra and provided with a free head for fastening a ligament end thereover.

Furthermore, rods 11, 12 of the apparatus of the present invention can be made in a single piece, the two-piece form of embodiment described above being preferable, however, when ligament retaining elements, such as screws, are used because, in this case, it precludes the need to reimplant said retaining elements after the preliminary operation for determining the tension of the stabilizer.

It should further be pointed out that the screws or other retaining elements 2,3 their caps 6 and rods 11,12 will preferably be made from a bio-compatible metallic alloy.

We claim:

1. An inter-vertebral stabilizer comprising at least one flexible ligament having an all-direction flexibility and at least two retaining elements, each retaining element having an implant portion configured to be implanted in a respective one of at least two successive vertebrae, a free head adjacent the implant portion for projecting from the respective vertebra when the implant portion is implanted in said verebra, and a lateral projection extending laterally from the head at a selected distance from the implant portion, said ligament being provided, at each end thereof, with a hanging means having a width less than the distance between the lateral projection and the implant portion for loose engagement around the free head of a respective one of the retaining elements, whereby the loose engagement of the ligament with the respective retaining element enables compensation for defects of a spine without hindering flexional and torsional movements thereof.

2. Inter-vertebral stabilizer according to claim 1, in which said at least one flexible ligament has the general form of a closed loop, the ends of which constitute said hanging means.

3. An inter-vertebral stabilizer according to claim 2 in which the lateral projection of each of the retaining elements is provided by a cap removably fitted on the head of the retaining element, said cap being radially over-dimensioned in relation to the head of the retaining element on which the cap is removably fitted, said cap preventing the ligament from slipping off the free head.

4. The inter-vertebral stabilizer according to claim 2 in which the lateral projection of each retaining element for retaining the ligament in loose engagement on the retaining element is unitary with the head thereof.

5. Inter-vertebral stabilizer according to claim 1, in which said at least one flexible ligament is provided, at each end thereof, with a closed loop constituting said hanging means.

6. An inter-vertebral stabilizer according to claim 5 in which the lateral projection of each of the retaining elements is provided by a cap removably fitted on the head of the retaining element, said cap being radially over-dimensioned in relation to the head of the retaining element on which the cap is removably fitted, said cap preventing the ligament from slipping off the free head.

7. The inter-vertebral stabilizer according to claim 5 in which the lateral projection of each retaining element for retaining the ligament in loose engagement on the retaining element is unitary with the head thereof.

8. Inter-vertebral stabilizer according to claim 1, in which each of the retaining elements is provided with a removable cap radially over-dimensioned in relation to the head of the retaining element on which the cap can be fitted, the cap comprising the lateral projection of the retaining element.

9. Inter-vertebral stabilizer according to claim 1 in which the lateral projection for retaining the ligament in loose engagement on the retaining element is unitary with the head thereof.

[10. A process for stabilizing a length of the spinal column comprising at least two successive vertebrae, said process comprising the steps of:

a) providing at least one flexible ligament having an all-direction flexibility and provided at each end with hanging means for loosely hanging the flexible ligament, b) providing at least two retaining elements, each of which has a free head and an implantation end, c) making a surgical incision in the patient's body in front of each vertebra of said length of the spinal column, d) implanting the implantation end of each retaining element in a respective one of said successive vertebrae, with said free head projecting from the vertebra after said retaining element has been implanted, e) installing said at least one flexible ligament on two respective successive retaining elements by passing the hanging means of each ligament end around the projecting free head of a respective one of said two successive retaining elements, so that said ligament end at least partly loosely encircles the free head of said retaining element thus permitting a movement of the ligament with respect to the retaining elements during selected flexional movements of the spinal column, said at least one ligament forming an inter-vertebral stabilizer together with the associated retaining elements.]

[11. The process of claim 10, in which said inter-vertebral stabilizer comprises a plurality of ligaments chained along the spinal column by means of the same plurality, plus one, of retaining elements.]

[12. The process of claim 10, further comprising the step of implanting at least one additional inter-vertebral stabilizer on the back face of said vertebrae, each of said stabilizers being placed on one respective side of the spine along the length of the spinal column to be stabilized.]

[13. The process of claim 10 comprising additional steps for determining the length at rest of said at least one ligament, said additional steps being performed between steps c) and d) and comprising successively:

implanting a rigid rod in each of the vertebrae concerned and at the point for implantation of the corresponding retaining element, with said rod extending out of the patient's body, immobilizing the two rods of each pair of adjacent rods at a predetermined distance from one another, performing a pain test by permitting a selected amount of time to elapse and determining whether a pain to be removed by the stabilizer persists, and in the event where the pain, the cause of which is to be removed by the stabilizer is persisting after the selected time has elapsed, modifying the distance between the rods by a selected pitch, immobilizing the rods in their new relative positions and carrying out the pain test again, by allowing the time to elapse and determining whether the pain persists, the steps of modifying the distance, immobilizing and testing for pain being repeated, if necessary until the pain disappears, the length at rest to be given to the ligament then being deduced from the value of the distance then attained between the two rods.]

[14. Apparatus for implement the process according to claim 13, characterized in that the apparatus comprises a set of at least two rods (11,12) each having an implantation end (2,3) for implanting in the respective vertebra (V1, V2), the rods being associated with at least one rigid link (15) of adjustable length for joining the rods at a point remote from their implantation ends.]

[15. Apparatus according to claim 14, characterized in that the implantation end of each rod is constituted by the corresponding retaining element (2,3) of the ligament of the said stabilizer and each of the rods (11,12) further comprises a removable extension piece (13) fitting onto the head (4) of said retaining element.]

[16. Apparatus according to claim 15, characterized in that the said length adjustable rigid link (15) comprises a thin bar (16) and two collars (17,18) that can be fitted respectively on the two rods (11,12) and are provided with means (20) for supporting the bar slidingly between them, an element (19) for locking the bar (16) being provided on each collar.]

[17. Apparatus according to claim 14, characterized in that it comprises an instrument (24) for determining the length at rest of the ligament, which is formed by two crossed legs (25,26) articulated on one another at their middle, the ends of the legs located on the same side of the articulation (27) each having a substantially semi-circular contacting portion (28,29).]

[18. An inter-vertebral stabilizer comprising at least one flexible ligament having an all-direction flexibility and at least two retaining elements, each retaining element having an implantation end implantable in a respective one of two successive vertebrae and a projecting free head, said ligament being provided at each end thereof with a hanging means for loosely engaging around the free head of a respective one of the retaining elements, at least two rods each having an end for temporary implantation in the respective vertebra, the rods being associated with at least one rigid link of adjustable length for joining the rods at a point remote from their implantation ends, whereby the rods and the link are employed for determining a proper relative position for stabilizing the vertebrae, and whereby the retaining elements and the ligament are employed for stabilizing the vertebrae in the relative position determined with the rods and the rigid link of adjustable length.]

[19. A stabilizer as in claim 18 wherein the implantation end of each said rod is defined by a corresponding one of the retaining elements, the rods being selectively removable from the retaining elements after determining the preferred relative position for stabilizing the vertebrae.]

[20. A stabilizer according to claim 18 wherein the rigid link of adjustable length comprises a pair of collars slidably engaged on the respective rods and a bar adjustably engagable by the collars for locking the rods in selected positions relative to one another.]

[21. A stabilizer according to claim 18 further comprising an instrument for determining the length at rest of the ligament, the instrument comprising a pair of crossed legs articulated to one another at their middle, the ends of the legs each having a substantially semi-circular contacting portion for engaging the rods at locations thereon generally adjacent the respective vertebrae.]

*22. An intervertebral stabilizer comprising:*

*at least one supple band made of a flexible plastics material having all-directional flexibility;*

*at least two retaining elements, each of said at least two retaining elements for being implanted in a respective one of at least two adjacent vertebrae;*

*said at least one supple band including hanging means for loosely engaging around two of said retaining elements, wherein said two retaining elements are movable toward each other by said loosely-engaged supple band; and*

*said at least one supple band being sized and configured such that the loose engagement and relative movement between said band and the retaining elements enable compensation for defects of a spine without hindering flexional and torsional movements thereof.*

*23. The intervertebral stabilizer according to claim 22, wherein said supple band has the form of a closed loop with spaced opposite ends constituting said hanging means.*

*24. The intervertebral stabilizer according to claim 22, wherein said supple band includes two spaced opposite ends each provided with a closed loop or ring constituting said hanging means.*

*25. The intervertebral stabilizer according to claims 22, 23 or 24, wherein each of said retaining elements has a free head for engaging said band.*

*26. The intervertebral stabilizer according to claim 25, wherein said free head of said retaining element is provided with a lateral projection, said lateral projection preventing said band from slipping off said free head.*

*27. The intervertebral stabilizer according to claim 26, wherein said retaining element is a screw.*

*28. The intervertebral stabilizer according to claim 25, wherein said retaining elements additionally comprise a cap removably fitted on said free head of said retaining element, said cap being radially over-dimensioned in relation to said free head of said retaining element on which said cap is removably fitted, said cap preventing said band from slipping off said free head.*

*29. The intervertebral stabilizer according to claim 28, wherein said retaining element is a screw.*

* * * * *